United States Patent
Gupta (10) Patent No.: US 7,717,859 B2
(45) Date of Patent: May 18, 2010

(54) METHOD AND COMBINATION ELECTRONIC COMMUNICATION AND MEDICAL DIAGNOSTIC APPARATUS FOR DETECTING/MONITORING NEUROPATHY

(75) Inventor: Ajay Gupta, Cerritos, CA (US)

(73) Assignee: Applied Medical Technologies LLC., Cerritos, CA (US)

(*) Notice: Subject to any disclaimer, the term of this patent is extended or adjusted under 35 U.S.C. 154(b) by 682 days.

(21) Appl. No.: 10/725,393

(22) Filed: Dec. 3, 2003

(65) Prior Publication Data

US 2005/0124910 A1 Jun. 9, 2005

(51) Int. Cl.
*A61B 5/00* (2006.01)

(52) U.S. Cl. ...................................... 600/552

(58) Field of Classification Search ................ 600/300, 600/301, 552, 553; 128/903
See application file for complete search history.

(56) References Cited

U.S. PATENT DOCUMENTS

| | | | |
|---|---|---|---|
| 5,002,065 A | 3/1991 | LaCourse et al. | |
| 5,208,987 A | 5/1993 | Christen | |
| 5,293,161 A * | 3/1994 | MacDonald et al. | 340/7.6 |
| 5,931,793 A | 8/1999 | Laudadio | |
| 6,287,252 B1 * | 9/2001 | Lugo | 600/300 |
| 6,478,736 B1 * | 11/2002 | Mault | 600/300 |
| 6,641,533 B2 * | 11/2003 | Causey et al. | 600/300 |
| 6,978,164 B2 * | 12/2005 | Vicendese | 455/575.6 |
| 2003/0060765 A1 * | 3/2003 | Campbell et al. | 604/131 |
| 2006/0152382 A1 * | 7/2006 | Hiltunen | 340/691.1 |

OTHER PUBLICATIONS

Mechaber, A. J. 1998, Postgraduate Medicine; 104(1):16.*
Lee, Po-Tsang et al. "High vibration perception threshold and autonomic dysfunction in hemodialysis patients with intradialysis hypotension", Kidney International 64:1089-1094 (2003).
Said, G. et al. "Different patterns of uremic polyneuropathy: Clinicopathologic study", Neurology 33:567-574 (1983).
Jennekens, F.G.I. et al. "Clinical Aspects of Uraemic Polyneuropathy", Nephron 8:414-426 (1971).
Rahman, M. et al. "How should peripheral neuropathy be assessed in people with diabetes in primary care? A population-based comparison of four measures", Diabetes UK. Diabetic Medicine 20:368-374 (2003).
Burns, T.M. et al. "Clinical versus quantitative vibration assessment: improving clinical performance", Journal of the Peripheral Nervous System 7:112-117 (2002).
Hilz, MJ et al. "Vibrameter testing facilitates the diagnosis of uremic and alcoholic polyneuropathy", Acta Neurol Scandinavica vol. 92 (6):486-490 (1995).
www.usneurologicals.com/tf.html, "US Neurologicals.com" (pp. 1-5).
www.senslab.com/vibrameter.html "Vibrameter" (2 pages).

* cited by examiner

*Primary Examiner*—Max Hindenburg
*Assistant Examiner*—Jonathan M Foreman
(74) *Attorney, Agent, or Firm*—Price, Heneveld, Cooper, DeWitt & Litton, LLP (57) ABSTRACT

A combination electronic communication and medical diagnostic apparatus includes a first component for transmitting or receiving a remote communication signal and a second component for generating vibration to be used in a medical diagnosis. The apparatus functions as a beeper/pager or cellular phone, as well as a medical diagnostic tool to detect and/or monitor neuropathy.

53 Claims, 6 Drawing Sheets

METHOD AND COMBINATION ELECTRONIC COMMUNICATION AND MEDICAL DIAGNOSTIC APPARATUS FOR DETECTING/MONITORING NEUROPATHY

BACKGROUND OF THE INVENTION

The present invention is generally directed to a medical diagnostic apparatus, and more particularly to a combination electronic communication and medical diagnostic apparatus which can be used as an electronic communication device, such as a beeper/pager or cellular phone, as well as a medical tool to detect and/or monitor neuropathy.

Diabetes is a very common disease that often leads to painful neuropathy. Symptomatic diabetic neuropathy is preceded by an asymptomatic phase during which nerve conduction by the large fibers is impaired, leading to an impairment of vibration perception. Vibration threshold is a continuous measure and by necessity, categorization into a binary outcome will mean setting of an arbitrary threshold. The $95^{th}$ and $97^{th}$ percentiles in non-diabetic populations have previously been used as thresholds for neuropathy. Vibration threshold is the most valid measure of nerve function in diabetic patients and has been used as a gold standard.

Vibration testing has long existed in various manners. For example, vibration threshold testing devices are currently being used which include two fixed probes in one or two boxes which are placed on a table or floor. The patient must touch them with the fingers or toes and indicate which one is vibrating. A further vibrating tool known as Biothesiometer, which is similar to vibrating devices sold in adult paraphernalia shops, is applied to an extremity and the vibration level is turned up until the patient can feel the vibration. The level is then read off a meter. These devices have also been computer driven.

A further example of vibration testing is by the utilization of a tuning fork, which can be applied to an extremity. A vibrating pen for detecting nerve impairment (neuropathy) is disclosed by Laudadio in U.S. Pat. No. 5,931,793. However, this is merely a pen-like device that does not incorporate the function of a beeper/pager or cellular phone. Furthermore, Laudadio's pen-like device measures vibration threshold as a binary outcome requiring setting of arbitrary thresholds used to define the severity of neuropathy as mild, moderate or severe.

A vibrating pen marketed by Solarwide Inc. sends a signal to indicate that the user has a call on a cellular phone but its use for the detection of neuropathy has not been described. Another form of vibrating pen known as a Wiggle Writer for children is disclosed in U.S. Pat. No. 5,208,987, which operates on a similar principle using an offset motor which causes the pen tip to draw circles.

A quantitative assessment of vibration threshold over a wide range of frequencies using various vibratory amplitude levels at vibration frequency is disclosed by Lacourse and McCoy in U.S. Pat. No. 5,002,065, in which they show that an increase in the perception threshold for vibration is the earliest detectable objective sign of carpal tunnel syndrome. Lee et al. have demonstrated the usefulness of determining vibration perception threshold in patients with end-stage renal disease as a measure of neuropathy (*Kidney International*, Vol 64, pp. 1089-1094, 2003). There are several other medical conditions, including alcohol abuse and vitamin deficiencies, that are associated with neuropathy.

Loss of large myelinated fibres is the most constant morphologic feature of neuropathy in patients with kidney failure or uremia. Impaired vibration perception of the toes is early and initially the only clinical sign of this peripheral neuropathy (G. Said, L. Boudier, J. Silva, J. Zingraff, T. Druecke: Different patterns of uremic polyneuropathy:clinicopathologic study. *Neurology* 33:567-574, 1983) and measurement of vibratory perception thresholds is more suitable to evaluate progression or recovery of uremic neuropathy than is measurement of nerve conduction velocity (Said et al, Id., and F G I Jennekens, E J Dorhout Mees, D Van der Most van spijk: Uremic polyneuropathy. *Nephron* 8: 414-426, 1971).

Although vibration threshold has been recognized as the gold standard for diabetic neuropathy, the investigators have been testing alternative measures as surrogates for the diagnosis of neuropathy (Rahman et al., *Diabetic Medicine* 20: 368-374, 2003), because the currently available devices used to determine vibration threshold are cumbersome, mostly used as research tools, and are not widely available in the primary care setting. In fact, majority of physicians, including the inventor of this invention have never seen the vibrameter devices, let alone use it.

In common clinical practice, the current standard of medical care is to use tuning fork as qualitative, or at best semi-quantitative tool, for diagnosing neuropathy. However, tuning forks are cumbersome, inaccurate, operator-dependent and consequently are used infrequently and only by a small minority of physicians. In addition, in using a tuning fork, physicians tend to underestimate or overestimate the loss of vibration sensation. In diabetic patients tuning fork overestimates loss of vibration, compared with quantitative vibration threshold using a vibrameter (T M Burns, A Taly, O'Brien, P J Dyck: Clinical versus quantitative vibration assessment: improving clinical performance. *Journal of the Peripheral Nervous System* 7:112-117, 2002). On the other hand, in uremic patients, tuning fork examination could demonstrate abnormalities in only 2.5% of patients whereas vibrameter was much more sensitive, detecting abnormalities in 47.5% of patients, similar to the 45% using nerve conduction velocity as the gold standard (M J Hilz, P Zimmermann, G Rosl, W Scheidler, J braun, B Stemper, B Neundorfer: Acta Neurol Scand. 92(6):486-90, 1995). Similarly, in the same study, in alcoholic patients tuning fork revealed abnormalities in only about 15% compared to 60% by vibrameter and about 35% by nerve conduction velocity. Therefore, it is evident that use of tuning fork is inaccurate and inadequate as a clinical tool for the detection of neuropathy in diabetic, uremic or alcoholic patients. On the other hand, vibrameter is more sensitive and specific for the detection of neuropathy since it employs quantitative stimuli, a broad range of stimulus magnitudes and null stimuli.

None of the diagnostic or monitoring devices described above, however, serve as electronic communication devices, either, for example, as a receiving pager or a cellular phone.

In view of the drawbacks associated with conventional tools and techniques, there is a need for a better and improved clinical tool for the detection and/or monitoring of neuropathy that is portable, can be easily carried by a physician or other health care professional on their person, and is more sensitive and specific compared to the tuning fork.

OBJECTS AND SUMMARY OF THE INVENTION

The principal object of the present invention is to provide an apparatus and method for detecting and/or monitoring neuropathy which overcomes the drawbacks associated with conventional devices and/or or techniques.

An object of the present invention is to provide a diagnostic method and apparatus for detecting and/or monitoring nerve impairment or neuropathy.

Another object of the present invention is to provide an easily portable neuropathy detection and/or monitoring apparatus which is incorporated in an electronic communication device, such as a beeper/pager or cellular phone that the vast majority of medical professionals routinely carry on their person.

Yet another object of the present invention is to provide a diagnostic apparatus for detecting and/or monitoring neuropathy which also functions as an electronic communication device, such as a beeper/pager or cellular phone.

Still yet another object of the present invention is to provide a compact and easy to carry apparatus which has the dual functions of electronic communication, such as a beeper/pager or cellular phone, and medical diagnostic tool for detecting and/or monitoring neuropathy. The apparatus allows a health care professional to perform simple and quick, yet accurate test to determine neuropathy in a subject. The apparatus produces instant results allowing the health care professional to refer the subject for further diagnostic evaluation when the primary cause of neuropathy is not apparent.

An additional object of the present invention is to provide a combination electronic communication and medical diagnostic apparatus which can be used to detect and/or monitor neuropathy caused by various medical conditions or ailments, such as diabetes, kidney failure or uremia, alcohol abuse, vitamin deficiencies, and carpal tunnel syndrome.

Yet an additional object of the present invention is to provide a combination electronic communication and medical diagnostic apparatus which can precisely quantitate and audibly or visibly indicate the vibration perception threshold (VPT), vibration disappearance threshold (VDT), and/or vibration threshold (VT), wherein VT is calculated as a composite of VPT and VDT. Quantitative measure of VT allows monitoring the progression of neuropathy over time.

A further object of the present invention is to provide a combination electronic communication and medical diagnostic apparatus which can be easily used by a person for self-diagnostic or self-evaluation purposes for detecting and/or monitoring neuropathy.

In summary, the main object of the present invention is to provide a neuropathy detection and/or monitoring apparatus which also functions as an electronic communication device, such as a beeper/pager or cellular phone. The apparatus, in view of its dual functionality, is easy and inexpensive to manufacture, and is further easy to carry by health care professionals who routinely carry beepers/pagers or cellular phones.

One of the above objects is met, in part, by the present invention which in one aspect includes a combination electronic communication and medical diagnostic apparatus, which comprises a first component for transmitting or receiving a remote communication signal and a second component for generating vibration to be used in a medical diagnosis.

Another aspect of the present invention includes a combination electronic communication and medical diagnostic apparatus, which comprises a device for generating vibration in first and second modes. One of the first and second modes is utilized in an electronic communication and the other of the first and second modes is utilized in a medical diagnosis.

Another aspect of the present invention includes an electronic communication apparatus for detecting neuropathy in a subject, which comprises a component for generating vibration of a fixed or variable magnitude, wherein when the apparatus is applied to a subject, threshold for the perception or disappearance of vibration can be determined as a measure of nerve function to detect neuropathy.

Another aspect of the present invention includes a medical diagnosis method, which comprises: providing a combination electronic communication and medical diagnostic apparatus, the apparatus including a first component for transmitting or receiving a remote electronic communication signal, and a second component for generating vibration to be used in a medical diagnosis; generating vibration and applying the apparatus to a subject; and diagnosing a medical condition based on detection or non-detection of vibration by the subject.

Another aspect of the present invention includes a method of detecting neuropathy in a subject, which comprises: providing a combination electronic communication and medical diagnostic apparatus, the apparatus including a first component for transmitting or receiving a remote electronic communication signal, and a second component for generating vibration to be used in detecting neuropathy; generating vibration of a predetermined magnitude or frequency as a threshold stimulus and applying the apparatus to a subject; and allowing the subject to indicate whether or not vibration can be detected; wherein the absence or presence of neuropathy is indicated by the subject's ability to detect or not detect the vibration.

Another aspect of the present invention includes a medical diagnostic method, which comprises: providing a combination electronic communication and medical diagnostic apparatus, the apparatus including a first component for transmitting or receiving a remote electronic communication signal, and a second component for generating vibration to be used in a medical diagnosis; applying the apparatus to a subject and generating vibration; and diagnosing a medical condition based on detection or non-detection of vibration by the subject.

Another aspect of the present invention includes a method of detecting neuropathy in a subject, which comprises: providing a combination electronic communication and medical diagnostic apparatus, the apparatus including a first component for transmitting or receiving a remote electronic communication signal, and a second component for generating vibration to be used in detecting neuropathy; applying the apparatus to a subject and generating vibration of a predetermined magnitude or frequency as a threshold stimulus; and allowing the subject to indicate whether or not vibration can be detected; wherein the absence or presence of neuropathy is indicated by the subject's ability to detect or not detect the vibration.

BRIEF DESCRIPTION OF THE DRAWINGS

The above and other objects, novel features and advantages of the present invention will become apparent from the following detailed description of the preferred embodiment(s) of the invention, as illustrated in the drawings, in which.

DETAILED DESCRIPTION OF THE PREFERRED EMBODIMENT(S) OF THE INVENTION

The present invention is based, at least in part, on the principle of creating a vibration by a small portable device, such as a beeper/pager or cellular phone. The vibrating device itself, or a probe extending from the device, is applied to the patient's extremity (finger, toe, tibia, wrist, face, etc.) and vibrates at a magnitude (or amplitude) and/or frequency which determines a specific level or threshold for the patient's ability to detect vibration. The magnitude, although preferably fixed, can be selected to be low (for minimal detection of threshold impairment), medium (to detect moderate neuropathy) or high (to detect severe neuropathy). If the patient can feel the vibration, set at a pre-selected level, the patient's threshold is lower than the level set. Conversely, if the patient cannot feel the vibration, the patient's threshold is higher than the level set.

However, vibration threshold is a continuous measure. Therefore, the present invention has been devised to precisely quantitate and display the vibration perception threshold (VPT), vibration disappearance threshold (VDT), and/or vibration threshold (VT) calculated as a composite measure of VPT and VDT. Quantitative measure of vibration threshold allows monitoring the progression of neuropathy over time. Vibration perception threshold (VPT) is known as the smallest stimulus magnitude (expressed in physical units) that is felt. To determine VPT, the stimulus strength is gradually increased from zero to the point where a vibratory sensation is first perceived. Subsequently, the stimulus strength is diminished from a supraliminal level until the sensation disappears. This indicates vibration disappearance threshold (VDT). Therefore, VDT is the largest stimulus magnitude (expressed in physical units) that is not felt. The average of VPT and VDT is known as the vibration threshold (VT).

Figure 1:
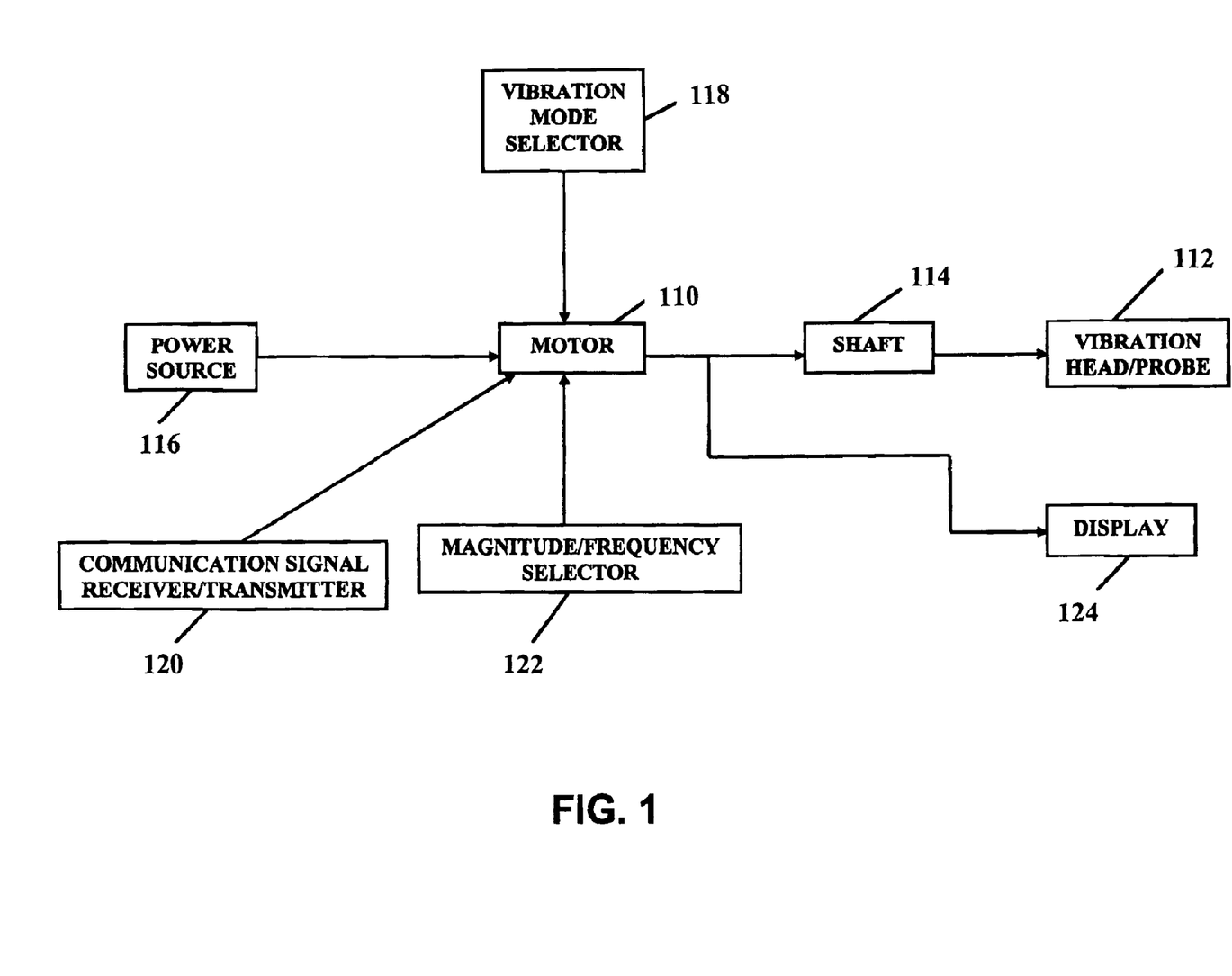
FIG. 1 is a schematic illustration of various components of a combination electronic communication and medical diagnostic apparatus of the present invention.

As illustrated schematically in FIG. 1, the communication and medical diagnostic apparatus CMD of the present invention includes a motor 110 for generating vibration, which is connected to a vibrating head 112 by a shaft 114. A power source 116, preferably a battery, provides electrical power to the motor 110. A vibration mode selector 118 allows a user to operate the apparatus CMD, either in the communication mode to receive or transmit signals via a communication signal receiver/transmitter 120 for paging, voice, data, etc., purposes, or in the diagnostic mode to detect or monitor neuropathy. In the communication mode, the motor 110 generates vibration at, for example, standard paging or beeping magnitude or frequency. In the diagnostic mode, however, the user can select to generate vibration at a desired magnitude (or amplitude) and/or frequency by activating the magnitude/frequency selector 122. In particular, the apparatus CMD is pre-programmed to generate vibration of a fixed or variable magnitude and/or frequency. The fixed magnitude would be of various preselected values that can be chosen by the user. Likewise, the variable magnitude would vary at preselected values in a linear, curvilinear, or step-like manner, that can also be chosen by the user. Along the same lines, the apparatus CMD is operable to generate vibration at various preselected fixed or variable frequencies.

The apparatus CMD is further provided with a display 124 to indicate the selected magnitude and/or frequency of the vibration. In addition to or as an alternative, the apparatus CMD may be provided with a mechanism to audibly indicate the vibration magnitude and/or frequency. Although not shown, the apparatus CMD may include a suitable memory chip and a microprocessor, or the like components for storing and/or processing the data, such as tested VPT, VDT, VT, etc. This would be particularly useful in monitoring the progress of treatment for neuropathy over time and/or to perform serial evaluation in, for example, hemodialysis patients. In addition, this would assist a person in detecting (or monitoring) neuropathy for self-diagnostic or self-evaluation purposes.

The apparatus CMD can be made of any suitable durable material, including an outer casing of plastic or metal of any color. The casing may contain a barrel, or a barrel within a barrel, to isolate the vibration from the outer casing. The battery(ies) would preferably be mounted inside a conducting aluminum plated cardboard barrel, which in turn would be mounted inside the outer casing or barrel(s) to provide a complete electrical circuit between an operating switch, battery(ies), and motor, or can be placed directly in the casing and wiring can be used to complete the circuit.

The vibrating head or probe 112 is preferably made of a plastic or metal material and may have a tubular or solid configuration projecting out from an end of the apparatus CMD.

The motor 110 can be a small DC motor with an offset weight on the shaft 114 or a piezoelectric or other transducer, capable of generating a vibration of a magnitude and/or frequency that is low enough not to be heard by the subject, but sufficient to allow detection.

Figure 2:
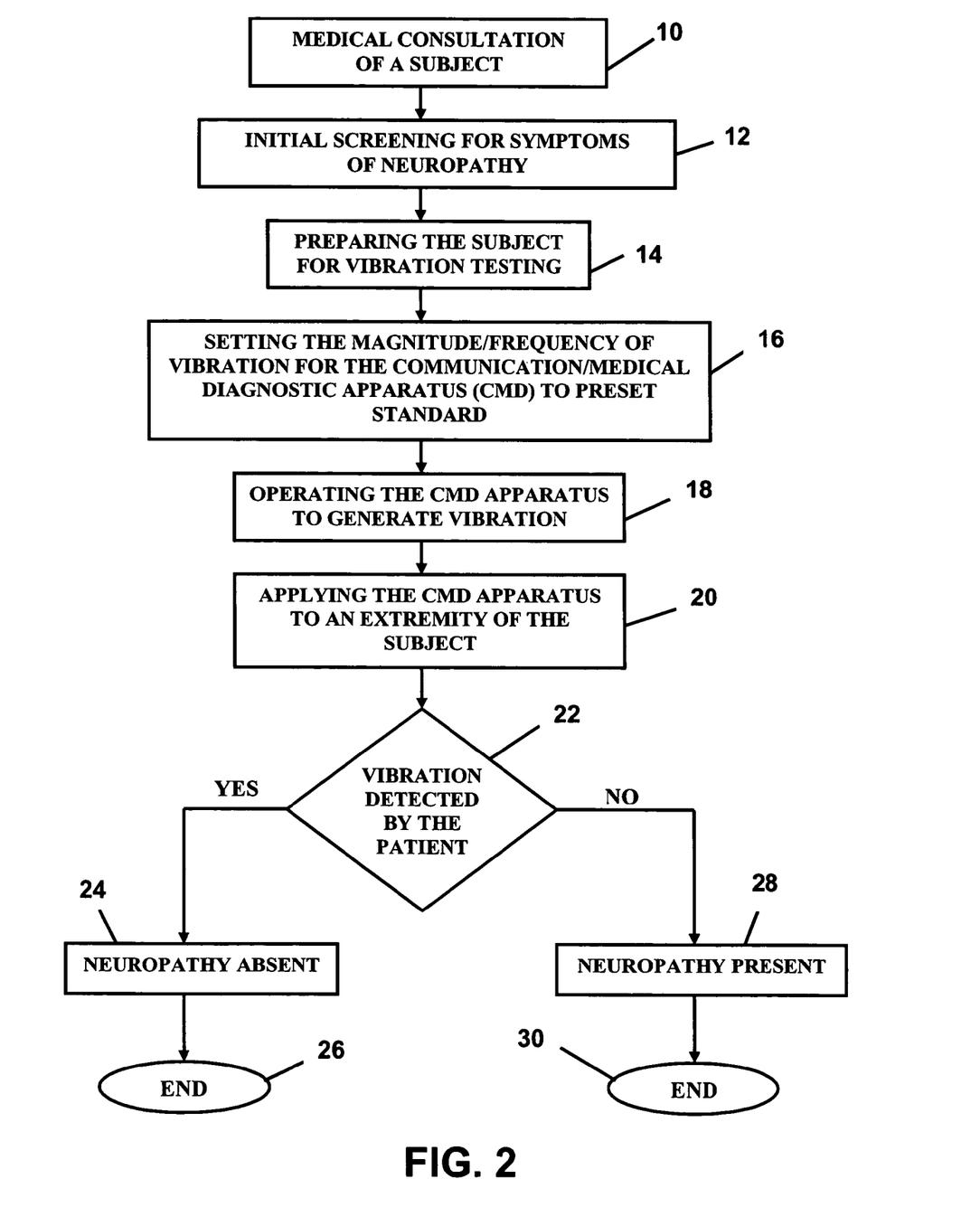
FIG. 2 illustrates a flow chart of a method of the invention for detecting neuropathy in a subject.
Figure 3:
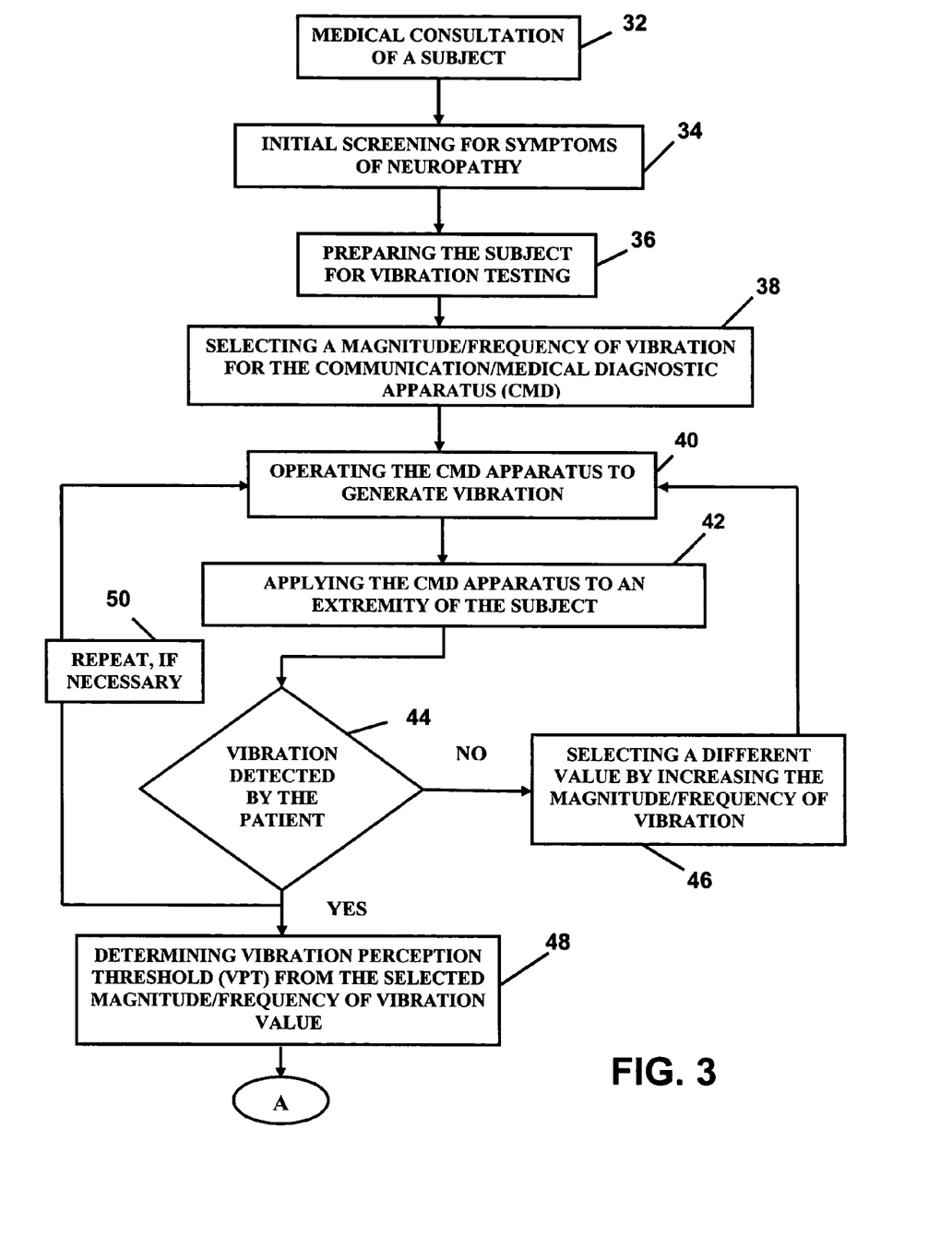
FIGS. 3-4 illustrate a flow chart of a method of the invention for determining vibration perception threshold (VPT) and determining and grading the severity of neuropathy in a subject.
Figure 4:
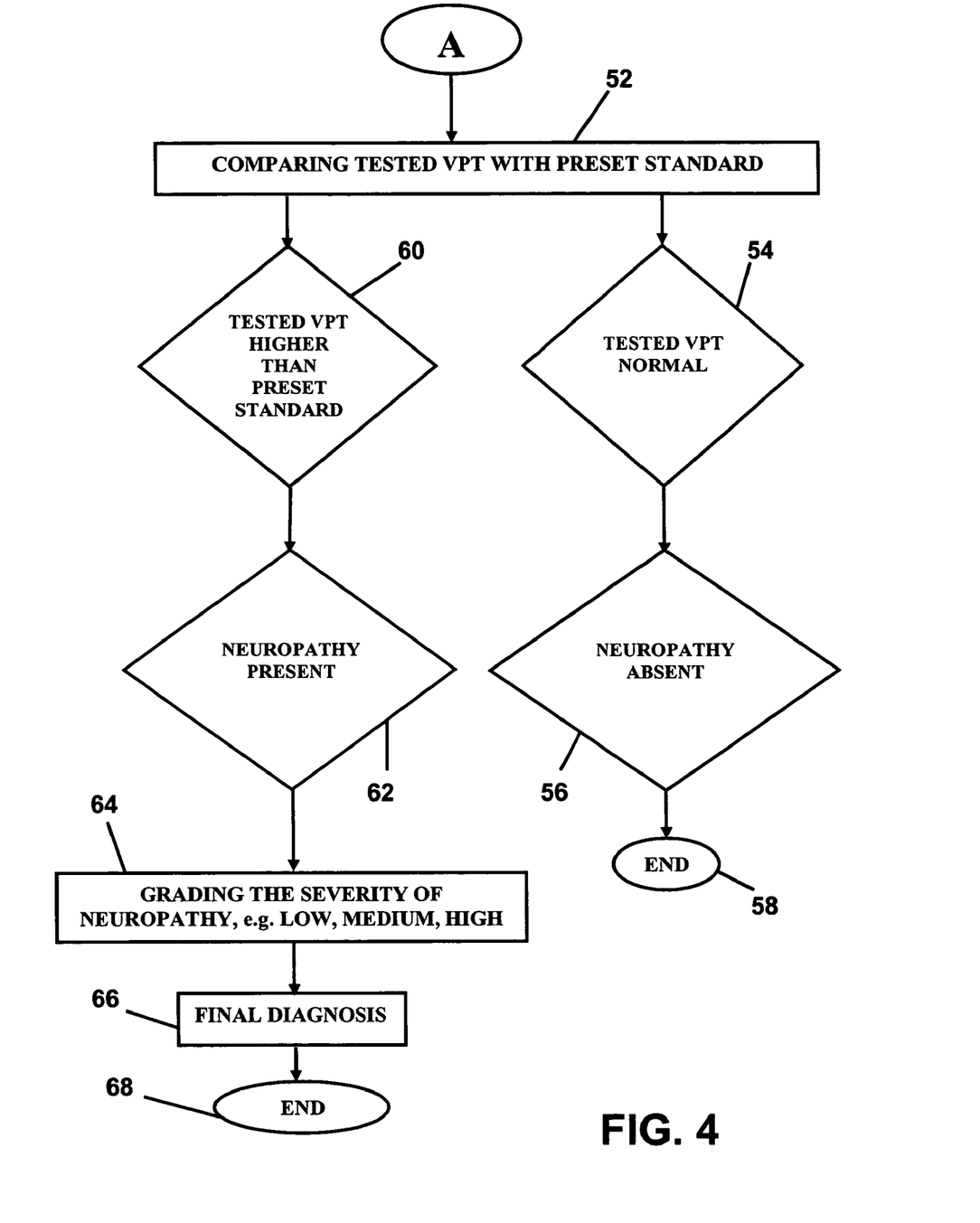
Figure 5:
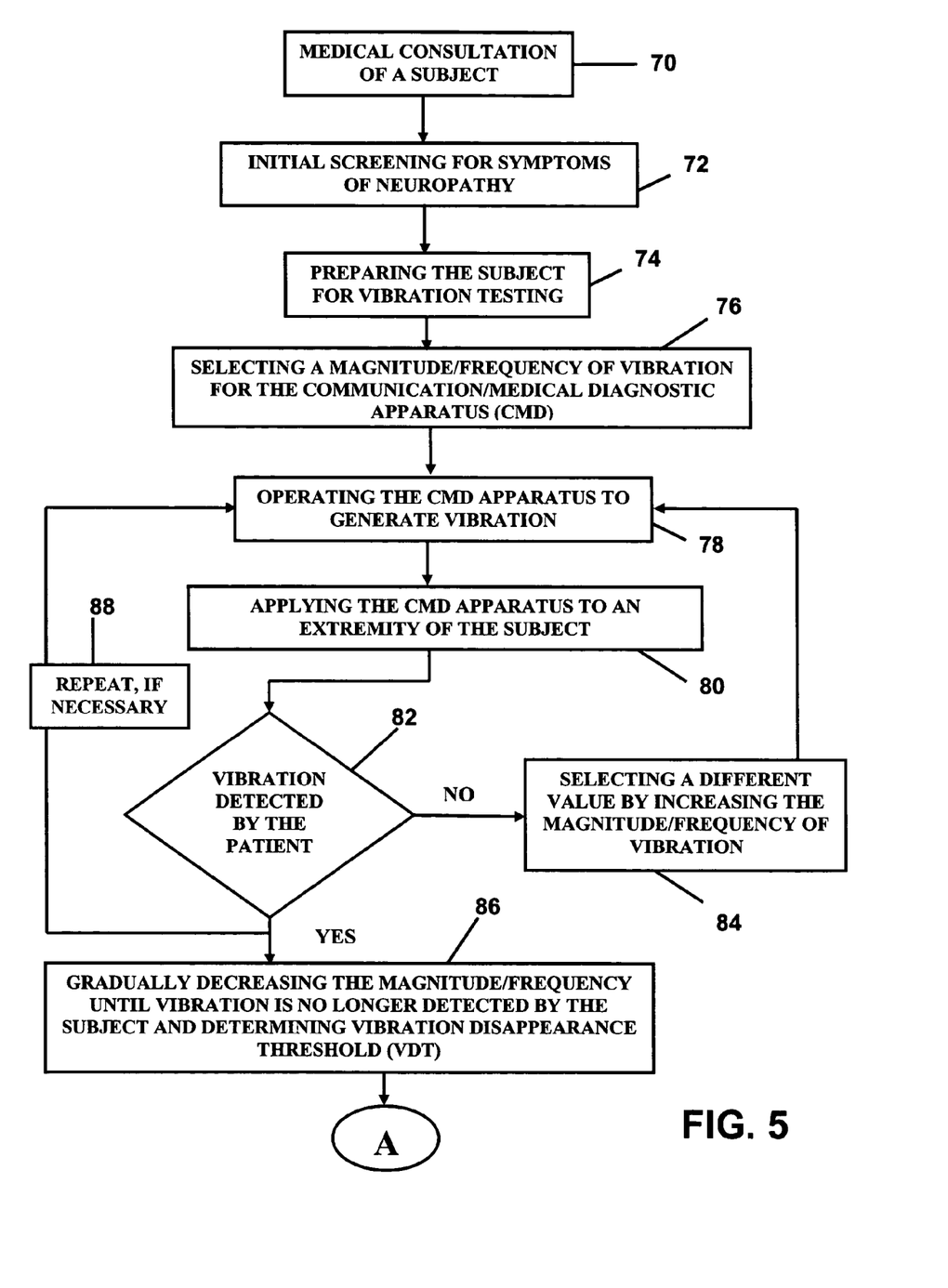
FIGS. 5-6 illustrate a flow chart of a method of the invention for determining vibration disappearance threshold (VDT) and determining and grading the severity of neuropathy in a subject.
Figure 6:
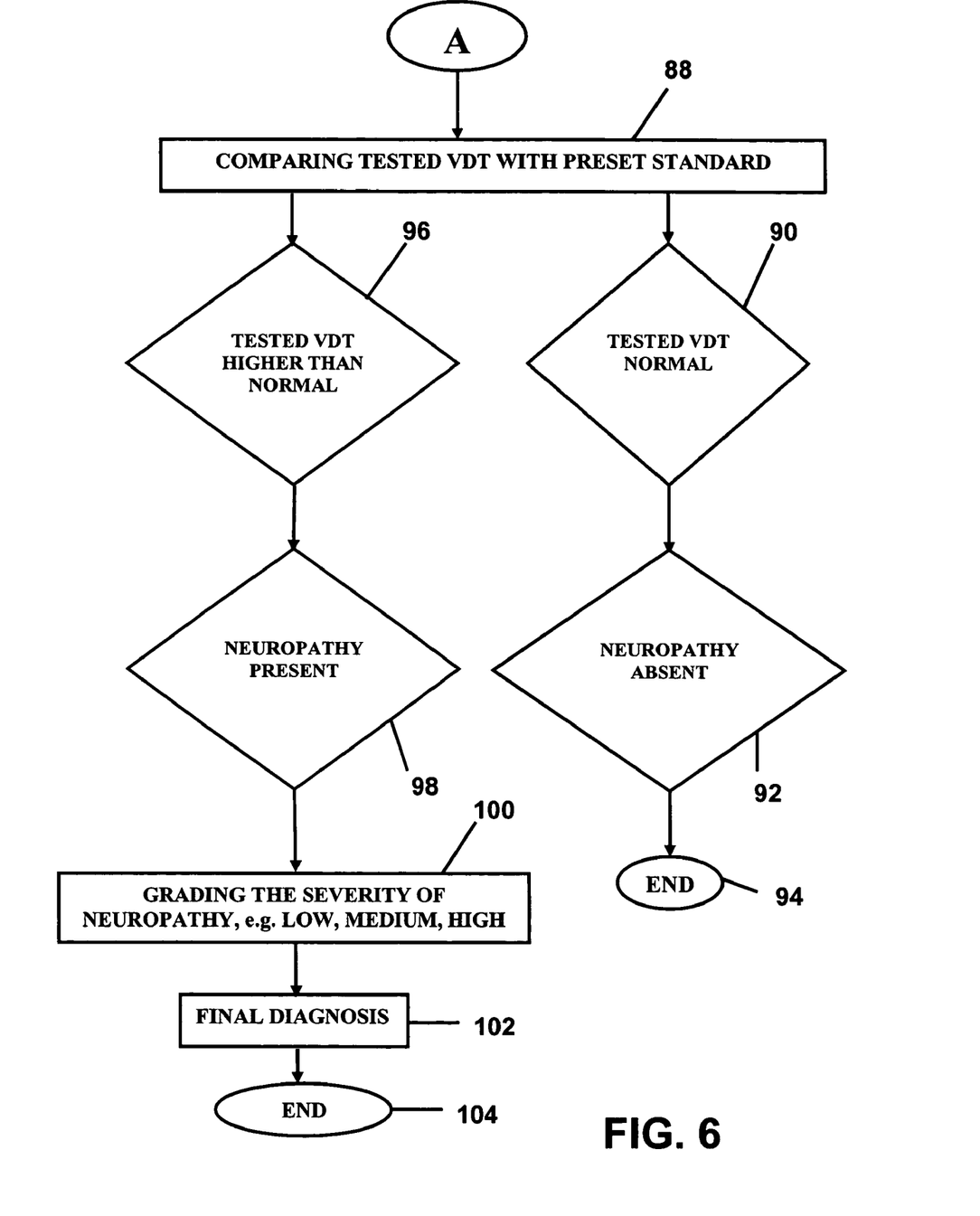

FIGS. 2-6 illustrate flow charts for carrying out various methods/procedures in accordance with the present invention. In particular, FIG. 2 illustrates a method for determining neuropathy in a subject. FIGS. 3-4 illustrate a method for determining vibration perception threshold (VPT) and determining and grading the severity of neuropathy in a subject. Likewise, FIGS. 5-6 illustrate a method for determining vibration disappearance threshold (VDT) and determining and grading the severity of neuropathy in a subject. Any of these procedures may be followed, as appropriate, in the event, a physician or other health care professional in a medical consultation of a subject suspects the presence or onset of a medical condition, ailment or disease that causes neuropathy or nerve impairment, such as diabetes, kidney failure or uremia, alcohol abuse, carpal tunnel syndrome, and/or vitamin deficiencies.

Referring to FIG. 2, after initial consultation (step 10), the subject is further screened for symptoms of neuropathy (step 12). If the medical professional feels that further testing would be beneficial, the subject is then prepared for vibration testing (step 14)). In order to test the subject's ability to detect vibration, the communication and medical diagnostic apparatus CMD of the present invention is set to the diagnostic mode by actuating the vibration mode selector 18, and a preset standard for magnitude or frequency is selected (step 16) by using the magnitude/frequency selector 22. For instance, the preset standard may correspond to the $95^{th}$ and $97^{th}$ percentiles in a non-diabetic population as threshold for neuropathy.

After the apparatus CMD has been set to a desired or preset magnitude or frequency, it is operated to generate vibration (step 18) and applied to an extremity of the subject (step 20). The subject is then asked whether or not he/she can detect the vibration (step 22). The detection of vibration by the subject would indicate the absence of neuropathy (step 24) and the procedure is ended (step 26). On the other hand, if the vibration is not detected by the subject, this would indicate the presence of neuropathy (step 28) and the procedure is ended (step 30).

FIGS. 3-4 illustrate a method for determining vibration perception threshold for a subject. As shown, a subject is initially consulted by a health care professional (step 32) and then screened for symptoms of neuropathy (step 34). The subject is then prepared for vibration testing (step 36) and the apparatus CMD is readied for testing by selecting a magnitude or frequency of vibration by actuating the magnitude/frequency selector 22 (step 38). The apparatus CMD is then operated to generate vibration (step 40) and applied to an extremity of the subject (step 42). The subject is then asked whether or not he/she can detect the vibration (step 44). If the subject cannot detect the vibration, the magnitude or frequency of vibration is gradually increased (step 46) and steps 40, 42 and 44 are repeated until the subject is able to detect the vibration. The value at which the subject is able to detect the vibration would indicate the vibration perception threshold (VPT) for the subject (step 48). In order to confirm the VPT value determined in step 48, or to obtain a more reliable value, the procedure may be repeated (step 50) to obtain several VPT values to obtain an average. The VPT value determined in step 48 is then compared with a preset standard or normal value (step 52). If the tested VPT (determined in step 48) is normal (step 54), the absence of neuropathy is indicated (step 56) and the procedure is ended. On the other hand, if the tested VPT is higher than normal (step 60), the presence of neuropathy is indicated (step 62). If the presence of neuropathy is indicated (step 62), the severity of neuropathy is graded, for example, low, medium, or high (step 64) based on the difference between the tested VPT and the preset standard. The final diagnosis is then rendered (step 66) and the procedure is ended (step 68).

FIGS. 5-6 illustrate a method for determining vibration disappearance threshold for a subject. As shown, a subject is initially consulted by a health care professional (step 70) and then screened for symptoms of neuropathy (step 72). The subject is then prepared for vibration testing (step 74) and a magnitude or frequency of vibration is selected on the apparatus CMD (step 76). The apparatus CMD is then operated to generate vibration (step 78) and applied to an extremity of the subject (step 80). The subject is then asked whether or not he/she can detect the vibration (step 82). If the subject cannot detect the vibration, the magnitude or frequency of vibration is gradually increased (step 84) and steps 78, 80 and 82 are repeated until the subject is able to detect the vibration. Once the subject is able to detect the vibration, the magnitude or frequency is then gradually decreased until the subject can no longer detect vibration (step 86). The value at which the subject can no longer detect the vibration, indicates the vibration disappearance threshold (VDT) for the subject. In order to confirm or obtain a more reliable VDT value, step 86 may be repeated to obtain several values to obtain an average (step 88). The tested VDT (step 86) is then compared with a preset standard or normal value (step 88). If the tested VDT is normal (step 90), the absence of neuropathy is indicated (step 92) and the procedure is ended (step 94). On the other hand, if the tested VDT is higher than normal (step 96) the presence of neuropathy is indicated (step 98), which is then graded, for example, low, medium, or high (step 100). The final diagnosis is then rendered (step 102) and the procedure is ended (step 104).

With respect to the above-described procedures, it is noted that the use of preset standard and/or prevalidated algorithms to test and to estimate threshold would greatly facilitate use of vibration testing to diagnose or monitor neuropathy in a clinical setting. These standards and/or algorithms would be created after determination of reference values based on a randomly chosen reference group that is free from neurological disease or disorder, neuropathy, or other diseases predisposed to cause neuropathy. This group would then be tested to determine a threshold value for the magnitude and/or frequency of vibration at which the vibration is normally detected. Based on these values, vibration magnitude and/or frequency would be expressed as percentiles for determining, monitoring or confirming neuropathy in a subject suspected of having this condition.

It is noted herewith that while in the methods illustrated in FIGS. 2-6, the apparatus CMD of the invention is applied to an extremity of the subject after generating vibration, it is within the scope of the invention to generate vibration after applying the apparatus CMD to the subject.

A standard diagnostic application of the present invention is for the neurodiagnostic assessment of hemodialysis patients for kidney failure. This provides a very sensitive predictor of morbidity and mortality in dialysis patients. Through manual recording or database functioning (i.e., storing and/or processing of test subject data) of the present apparatus, a comparison of measures from one testing period to another is performed in order to assess overall neurological health of an individual with respect to their health condition (i.e., kidney dialysis patient). For example, uremic patients are routinely evaluated every three months. By using this automatic diagnostic feature of the present apparatus, serial measurements from uremic patients may be compared and an estimation of the neurological stability of the patient may be provided as part of the diagnostic output of the present apparatus. Such information would be valuable to a nephrologist in determining whether to maintain the present level of kidney dialysis or increase dialysis dose for the patient being evaluated. The ability to perform such serial evaluations is an important feature of the present invention.

Although vibratory testing devices have been available for some time and vibrating pens are known, the present invention represents the first time that a medical device has been proposed that tests for vibration perception and disappearance thresholds utilizing an electronic communication and medical diagnostic apparatus. The usefulness of the invention is apparent considering that billions of dollars are spent each year on diabetic foot problems related to diabetic neuropathy. Yet a device such as of the invention has not yet been proposed. However, if a simple, inexpensive device such as the CMD apparatus of the invention, were available to nurses, physicians, and other health care professionals, neuropathy could be detected early and many ulcers, infections, and amputations might be avoided by instituting proper foot care early. In addition, once detected, the treatment of neuropathy could be easily monitored by using the apparatus CMD of the invention. In addition, since the apparatus CMD could be easily used by a subject for self-diagnostic or self-monitoring purposes, early self-detection and improved monitoring would result leading to reduction in overall health care spending and better well-being for the patients.

While this invention has been described as having preferred sequences, ranges, steps, materials, structures, features, and/or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

What is claimed is:

1. A portable multi-functional electronic communication and medical diagnostic device operable in a first operational mode as one or more of a cellular phone, pager, and beeper, and in a second operational mode for use in a medical diagnosis, the device comprising:
   an outer casing;
   a vibratory component disposed within the outer casing for generating vibration at one or more of an available plurality of magnitudes, the vibratory component being adapted to generate vibration in the first operational mode of the device in response to a remote wireless signal when the device is operated as one or more of a cellular phone, pager, and beeper, the vibratory component being further adapted to generate vibration in the second operational mode of the device at one or more selected magnitudes when the device is used in a medical diagnosis;
   a mode selector for selecting between the first operational mode of the device and the second operational mode of the device; and
   a display for indicating the magnitude of vibration being generated by the vibratory component in the second mode.

2. The device of claim 1, further comprising a selector for selecting the one or more magnitudes of vibration in the second mode.

3. The device of claim 2, wherein the component generates vibration of a fixed magnitude in the second mode.

4. The device of claim 2, wherein the component generates a plurality of sets of vibration each of a fixed magnitude in the second mode.

5. The device of claim 2, wherein the component generates vibration of a variable magnitude in the second mode.

6. The device of claim 2, wherein the magnitude is variable in a linear, curvilinear, or step-like manner.

7. The device of claim 1, wherein the device can be used in the second mode to determine one or more of a vibration perception threshold, a vibration disappearance threshold, and a vibration threshold, the device further comprising one or both of an audio display and a visual display to indicate one or more of the vibration perception threshold, the vibration disappearance threshold, and the vibration threshold.

8. The device of claim 7, further comprising at least one component for storing and/or processing data including one or more of the vibration perception threshold, the vibration disappearance threshold, and the vibration threshold.

9. The device of claim 1, the vibratory component being further adapted to generate vibration a selected one or more of an available plurality of frequencies, the device further comprising a selector for selecting one or more frequencies of vibration in the second mode.

10. The device of claim 9, wherein the component generates vibration at a fixed frequency in the second mode.

11. The device of claim 9, wherein the component generates a plurality of sets of vibration each at a fixed frequency in the second mode.

12. The device of claim 9, wherein the component generates vibration at a variable frequency in the second mode.

13. The device of claim 1, wherein the device is adapted to be applied to several extremities of a subject, one extremity at a time, the extremities including a finger, a toe, a tibia, a wrist, and a face.

14. The device of claim 1, wherein the vibratory component comprises a motor for generating vibration, a vibrating head adapted to be applied to the extremity of a subject, and a shaft transmitting vibration from the motor to the vibrating head.

15. The device of claim 14, wherein the motor is a DC motor and the shaft comprises an offset weight thereon.

16. The device of claim 14, wherein the motor is a piezoelectric transducer.

17. The device of claim 1, further comprising a mechanism for audibly indicating one or both of the magnitude of vibration and the frequency of vibration being generated by the vibratory component in the second mode.

18. The device of claim 1, wherein the outer casing is isolated from the vibration generated by the vibratory component.

19. A portable multi-functional electronic communication and medical diagnostic device operable in a first mode and in a second mode, comprising:
   an outer casing;
   a vibratory component disposed within the outer casing for generating vibration at one or more of an available plurality of magnitudes and at least one frequency, the vibratory component being adapted to generate vibration at a preprogrammed magnitude and frequency in the first mode of the device, the component being adapted to generate vibration at a frequency and at one or more selected magnitudes in the second mode of the device;
   a selector for selecting one or the other of said first and second modes;
   a probe from transmitting vibration from the vibratory component to a subject; and
   a display for indicating one or more of the magnitude of vibration and the frequency of vibration in the second mode;
   wherein in the first mode the device functions as a portable electronic device comprising one or more of a cellular phone, pager, and beeper; and
   wherein in the second mode the device operates to detect the presence or absence of neuropathy in a subject.

20. The device of claim 19, wherein the selected magnitude comprises a fixed magnitude.

21. The device of claim 20, wherein the selected magnitude comprises a plurality of sets of vibrations each of a fixed magnitude.

22. The device of claim 19, wherein the selected magnitude comprises a variable magnitude.

23. The device of claim 19, wherein the selected magnitude varies in a linear, curvilinear, or step-like manner.

24. The device of claim 19, wherein the selected frequency comprises a fixed frequency.

25. The device of claim 19, wherein the selected frequency comprises a plurality of sets of vibration each at a fixed frequency.

26. The device of claim 19, wherein the selected frequency comprises a variable frequency.

27. The device of claim, 19, wherein the probe can be used to determine one or more of a vibration perception threshold, a vibration disappearance threshold, and a vibration threshold, the device further comprising one or both of an audio display and a visual display to indicate one or more of the vibration perception threshold, the vibration disappearance threshold, and the vibration threshold.

28. The device of claim 27, further comprising at least one component for storing and/or processing data including one or more of the vibration perception threshold, the vibration disappearance threshold, and the vibration threshold.

29. A medical diagnosis method, comprising:
providing a portable multi-functional electronic communication and medical diagnostic device selectively operable in either a first operational mode or a second operational mode, the device comprising a component for generating vibration at one or more of an available plurality of magnitudes, an outer casing enclosing the component, the component being adapted to generate vibration in response to a remote wireless signal in the first mode when the device is operated as an electronic communication device comprising one or more of a cellular phone, pager, and beeper, the component being further adapted to generate vibration in the second mode when the device is used for medical diagnosis;
selecting the second mode of the device;
selecting one or more magnitudes of vibration to be used in medical diagnosis;
generating vibration;
applying the probe to a subject; and
diagnosing a medical condition based on detection or non-detection of vibration by the subject.

30. The method of claim 29, further comprising determining a threshold for the subject's ability to detect vibration based on whether the subject can detect vibration at the selected one or more magnitudes of vibration.

31. The method of claim 30, wherein the threshold is graded low if the subject detects vibration, and high if the subject cannot detect vibration.

32. The method of claim 30, further comprising increasing the magnitude of vibration and determining a vibration perception threshold based on the subject's ability to detect vibration while the magnitude of vibration is increased.

33. The method of claim 32, wherein the vibration perception threshold is graded low, medium, or high when compared to a preset standard thereby indicating the severity of the medical condition.

34. The method of claim 30, further comprising decreasing the magnitude of vibration and determining a vibration disappearance threshold based on the subject's ability to no longer detect vibration while the magnitude of vibration is decreased.

35. The method of claim 34, wherein the vibration disappearance threshold is graded low, medium, or high when compared to a preset standard thereby indicating the severity of the medical condition.

36. The method of claim 30, wherein the magnitude of vibration is fixed.

37. The method of claim 30, wherein the magnitude of vibration is variable in a linear, curvilinear, or step-like manner.

38. The method of claim 29, wherein the medical condition comprises neuropathy.

39. The method of claim 38, wherein the step of generating vibration comprises generating vibration of a magnitude corresponding to about the 95th-97th percentiles of a threshold magnitude of vibration for neuropathy in a normal population.

40. The method of claim 39, wherein detection of vibration by the subject indicates an absence of neuropathy, and non-detection indicates a presence of neuropathy.

41. The method of claim 38, wherein the device is applied to an extremity of the subject.

42. The method of claim 29, wherein the outer casing is isolated from the vibration generated by the vibratory component.

43. A method of detecting neuropathy in a subject, comprising:
providing a portable multi-functional electronic communication and medical diagnostic device selectively operable in either a first operational mode or a second operational mode, the device comprising a component for generating vibration at one or more of an available plurality of magnitudes, an outer casing enclosing the component and a probe extending outwardly from the outer casing, the probe being caused to vibrate by the component, the component being adapted to generate vibration in response to a remote wireless signal in the first mode when the device is operated as an electronic communication device comprising one or more of a cellular phone, pager, and beeper, the component being further adapted to generate vibration at a selected one or more selected magnitudes in the second mode when the device is used for medical diagnosis;
selecting the second mode of the device;
generating vibration and applying the probe to a subject;
allowing the subject to indicate whether or not vibration can be detected; and
determining the absence or presence of neuropathy by the subject's ability to detect or not detect the vibration.

44. The method of claim 43, wherein the magnitude of vibration generated by the component corresponds to about the 95th-97th percentiles of a threshold magnitude of vibration for neuropathy in a normal population.

45. The method of claim 43, wherein the step of generating vibration comprises generating vibration of a fixed magnitude.

46. The method of claim 43, wherein the step of generating vibration comprises generating vibration of a variable magnitude.

47. The method of claim 46, wherein comprising increasing the magnitude of vibration and determining a vibration perception threshold based on the subject's ability to detect vibration while the magnitude of vibration is increased.

48. The method of claim 47, wherein the vibration perception threshold is graded low, medium, or high when compared to a preset standard thereby indicating the severity of neuropathy.

49. The method of claim 46, further comprising decreasing the magnitude of vibration and determining a vibration disappearance threshold for the subject's ability to no longer detect vibration while the magnitude of vibration is decreased.

50. The method of claim 49, wherein the vibration disappearance threshold is graded low, medium, or high when compared to a preset standard thereby indicating the severity of neuropathy.

51. A medical diagnosis method, comprising:
providing a portable multi-functional electronic communication and medical diagnostic device selectively operable in either a first operational mode or a second operational mode, the device comprising a component for generating vibration at one or more of an available plurality of magnitudes, an outer casing enclosing the component and a probe extending outwardly from the outer casing, the probe being caused to vibrate by the component, the component being adapted to generate vibration in response to a remote wireless signal in a first mode when the device is operated as an electronic communication device comprising one or more of a cellular phone, pager, and beeper, the component being further adapted to generate vibration in the second mode when the device is used for medical diagnosis;
selecting the second mode of the device;

applying the probe to a subject and generating vibration at one or more selected magnitudes; and diagnosing a medical condition based on detection or non-detection of vibration by the subject.

52. A method of detecting neuropathy in a subject, comprising:

providing a portable multi-functional electronic communication and medical diagnostic device operable in a first operational mode and a second operational mode, the device comprising a component for generating vibration at a one or more of an available plurality of magnitudes, an outer casing enclosing the component, and a probe extending outwardly from the outer casing, the probe being caused to vibrate by the component, the component being adapted to generate vibration in response to a remote wireless signal in the first mode when the device is operated as an electronic communication device comprising one or more of a cellular phone, pager, beeper, the component, being further adapted to generate vibration at in the second mode when the device is used for medical diagnosis;

selecting the second mode of the device;

applying the probe to a subject and generating vibration at one or more selected magnitudes;

allowing the subject to indicate whether or not vibration can be detected; and determining the absence or presence of neuropathy by the subject's ability to detect or not detect the vibration.

53. A portable electronic device comprising:

an outer casing;

a vibratory component disposed within the outer casing for generating vibration having at least one magnitude selectable from an available plurality of magnitudes;

a mode selector for selecting between a first mode of the device and a second mode of the device;

a magnitude selector for selecting at least one magnitude of vibration of the vibratory component in the second mode, wherein the selected at least one magnitude is a fixed magnitude, a linearly increasing or decreasing magnitude, a curvilinearly increasing or decreasing magnitude, a step-wise increasing or decreasing magnitude, or a combination thereof; and a display for indicating the magnitude of vibration generated by the vibratory component in the second mode;

wherein in the first mode the device is operable as at least one of a cellular phone, a pager, and a beeper, and the vibratory component generates vibration in response to a remote wireless signal; and wherein in the second mode the device is operable as a medical diagnostic device and the vibratory component generates vibration of the at least one magnitude of vibration selected by the magnitude selector.

* * * * *

UNITED STATES PATENT AND TRADEMARK OFFICE
CERTIFICATE OF CORRECTION

PATENT NO.        : 7,717,859 B2
APPLICATION NO. : 10/725393
DATED             : May 18, 2010
INVENTOR(S)       : Gupta It is certified that error appears in the above-identified patent and that said Letters Patent is hereby corrected as shown below:

Col. 2, lines 18-20,
"fact, majority of physicians, including the inventor of this invention have never seen the vibrameter devices, let alone use it." should be --fact, a majority of physicians, including the inventor of this invention, have never seen the vibrameter devices, let alone used it.--

Col. 2, line 22,
"use tuning" should be --use a tuning--;

Col. 2, line 28,
"patients tuning" should be --patients a tuning--;

Col. 2, line 39,
"braun" should be --Braun--;

Col. 2, line 42,
Before "tuning fork" insert --a--;

Col. 2, line 44,
Before "tuning fork" insert --a--;

Col. 2, line 67,
"and/or or techniques" should be --and/or techniques--;

Col. 3, line 19,
"perform simple" should be --perform a simple--;

Col. 6, line 52,
"14))." should be --14).--;

Signed and Sealed this

Second Day of November, 2010

David J. Kappos
*Director of the United States Patent and Trademark Office*

Col. 8, line 46,

"such as of" should be --such as that of--;

Col. 8, line 66,

"come" should be --coming--;

Col. 9, line 1,

"fall" should be --falling--;

Col. 9, claim 9, line 53, after "vibration" insert --at--;

Col. 10, claim 19, line 31,

"from" should be --for--;

Col. 10, claim 27, line 57,

"claim, 19," should be --claim 19--; and

Col. 13, claim 52, line 21, after "vibration" delete "at".